(12) United States Patent
Clarke

(10) Patent No.: US 6,557,550 B1
(45) Date of Patent: May 6, 2003

(54) INHALATION DEVICE

(75) Inventor: Alastair Robert Clarke, West Malling (GB)

(73) Assignee: Aventis Pharma Limited, West Malling (GB)

( * ) Notice: Subject to any disclaimer, the term of this patent is extended or adjusted under 35 U.S.C. 154(b) by 0 days.

(21) Appl. No.: 09/552,103

(22) Filed: Apr. 19, 2000

Related U.S. Application Data

(63) Continuation of application No. PCT/GB98/03170, filed on Oct. 23, 1998.

(51) Int. Cl.⁷ ............................................. A61M 15/00
(52) U.S. Cl. ............................. 128/203.15; 128/203.21
(58) Field of Search ...................... 128/203.15, 203.21; 222/342, 80; 277/530, 631, 647

(56) References Cited

U.S. PATENT DOCUMENTS

| | | | | |
|---|---|---|---|---|
| 792,514 A | * | 6/1905 | Gill | 277/530 |
| 793,463 A | * | 6/1905 | McDonald | 277/647 |
| 1,942,489 A | * | 1/1934 | Pfefferle | 277/631 |
| 2,081,040 A | * | 5/1937 | King | 277/647 |
| 2,610,846 A | * | 9/1952 | Hanna | 277/530 |
| 3,028,166 A | * | 4/1962 | Adamson | 277/647 |
| 3,207,524 A | * | 9/1965 | Trbovich | 277/647 |
| 3,572,729 A | * | 3/1971 | Hodil, Jr. | 277/647 |
| 3,637,223 A | * | 1/1972 | Weber | 277/647 |
| 3,690,682 A | * | 9/1972 | Ferrill | 277/647 |
| 3,713,660 A | * | 1/1973 | Luthe | 277/647 |
| 4,805,811 A | * | 2/1989 | Wetterlin | 222/342 |
| 5,176,132 A | * | 1/1993 | Drought et al. | 128/203.15 |
| 5,341,800 A | | 8/1994 | Clark et al. | 128/203.15 |
| 5,394,868 A | * | 3/1995 | Ambrosio et al. | 128/203.15 |
| 5,429,122 A | * | 7/1995 | Zanen et al. | 128/203.15 |
| 5,435,282 A | * | 7/1995 | Haber et al. | 128/203.15 |
| 5,475,467 A | | 12/1995 | Watanabe et al. | 355/200 |
| 5,482,946 A | | 1/1996 | Clark et al. | 514/291 |
| 5,493,954 A | * | 2/1996 | Kostohris et al. | 277/647 |
| 5,538,999 A | | 7/1996 | Clark et al. | 514/65.3 |
| 5,628,307 A | | 5/1997 | Clark et al. | 128/203.15 |
| 5,673,685 A | | 10/1997 | Heide et al. | 128/203.15 |
| 5,678,538 A | * | 10/1997 | Drought | 128/203.21 |
| 6,026,774 A | * | 2/2000 | Kajihara et al. | 277/647 |
| 6,054,082 A | * | 4/2000 | Heide et al. | 128/203.21 |
| 6,286,840 B1 | * | 9/2001 | Zettel | 277/647 |

FOREIGN PATENT DOCUMENTS

| | | |
|---|---|---|
| EP | 0 407 028 | 9/1994 |
| EP | 0 691 865 | 5/1997 |

\* cited by examiner

*Primary Examiner*—Aaron J. Lewis
(74) *Attorney, Agent, or Firm*—Peter L. Dolan

(57) ABSTRACT

An inhalation device which contains powdered medicament in the form of a medicament compact is provided with a seal comprising a partial ring between the outer wall and inner mandrel of the medicament compact chamber. The medicament is dispensed by abrading the medicament compact by turning the compact relative to the inner mandrel against a blade. Despite only extending around part of the circumference of the mandrel the seal prevents leakage of loose powder from the compact chamber to the rest of the device. The sealing means also provides a frictional braking force on the medicament reservoir sufficient to prevent movement of the medicament reservoir when the drive mechanism for the reservoir is returning to its starting position without making the device difficult to operate by a child or infirm adult.

15 Claims, 5 Drawing Sheets

INHALATION DEVICE

CROSS REFERENCE TO RELATED APPLICATIONS

This is a continuation of International Patent Application No. PCT/GB98/03170, filed Oct. 23, 1998, which claims priority from Great Britain Patent application No. 9722285.5, filed Oct. 23, 1997.

This invention relates to a device for the administration of powdered medicaments by inhalation, more particularly to a multiple-dose inhalation device with metering means for dispensing pre-determined doses from a medicament reservoir.

European Patent 407028 discloses a multiple-dose inhalation device in which a dose of medicament is metered by abrading a fixed volume from a compacted body of powdered medicament. In a preferred embodiment of this device the compacted body of medicament comprises a cylinder which is held within a reservoir and which fits over an inner mandrel. The mandrel provides support for some or all of the medicament compact and provides an axis around which the reservoir and compact is turned in order to abrade a dose of medicament from the compact. The metered dose is then entrained in a through-going pathway of the device and is inhaled by the patient, the means for abrading being, for example, a helical blade.

The device of EP 407028 was improved in EP 691865 by providing a shuttering system to isolate the compacted body of medicament from the through-going pathway of the device. However, during transport powder still tended to leak from the medicament compact to the outer mechanism.

We have now found that this leakage can be greatly reduced by provision of a partial sealing means between the medicament reservoir and the inner mandrel of the inhalation device. Surprisingly it has been found that although a gap must be left in the sealing means in order to accommodate the pathway between the medicament reservoir and the dispersion chamber leakage is substantially reduced. Another advantage of the seal is that it provides a frictional brake which allows the ratchet mechanism rotating the medicament reservoir to cause abrasion of the medicament compact therein to return to its starting position without concomitant movement of the medicament reservoir.

Thus, according to one aspect of the invention, there is provided a medicament inhalation device including a housing having a through-going pathway connecting an air inlet with an air outlet, a medicament reservoir adapted to receive a compacted body of powdered medicament, an inner mandrel around which the medicament reservoir rotates and metering means for dispensing a predetermined dose of medicament from the reservoir into the pathway, the metering means including means for abrading the compacted body; characterised in that there is provided between the medicament reservoir and the inner mandrel of the device a sealing means extending round less than 360° of the mandrel.

In a further aspect of the invention the sealing means is adapted to provide a frictional braking force on the medicament reservoir sufficient to prevent movement of the medicament reservoir when the ratchet mechanism designed to cause rotation of the reservoir is returning to its starting position but which force is not so large as to make the device difficult to operate by a child or infirm adult. Typically this force will comprise a torque of between 0.1 and 0.6 Newton meters (Nm), preferably between 0.2 and 0.5 Nm and most preferably about 0.4 Nm.

The sealing means may be produced as an integral feature of the inner mandrel in a single production operation. This may be particularly advantageous when the material of construction of the mandrel is such that the sealing means feature is suitably resilient to produce the required seal and/or frictional braking effects.

The sealing means may be added to the mandrel during production by any standard process method, allowing the mandrel body and sealing ring to be formed from different materials. One such method is known as insert moulding. In insert moulding the mandrel body is formed by a standard moulding process. The mandrel body is transferred to a separate tool where the sealing means is moulded into position on the mandrel body. This process gives a good mechanical fit between the mandrel body and the sealing means but no adhesive or chemical bond. A second method is co-moulding. The mandrel body is formed by a standard moulding process. Co-incident with or slightly after the formation of the mandrel the sealing means is moulded in place using the same machine. In this process a chemical or adhesive bond is formed between the sealing means and the mandrel body.

Alternatively the sealing means may comprise a separate partial sealing ring. It is preferred that the sealing ring be formed in a single moulding process rather than being provided as a complete ring and cut to size.

The sealing means may conveniently be produced from any suitable resilient material. It is important that the material be compatible with the medicament and excipients used to form the medicament compact. ABS or Polyolefin plastic materials are preferred and a particularly preferred material is polypropylene.

The ring may be of any cross sectional shape capable of providing a good seal. A particularly advantageous shape for the cross section is a generally 'V' shape with the point of the 'V' aligned to face the medicament compact. Preferably the arm of the 'V' next to the inner mandrel is flush with the mandrel. The section of the ring in contact with the inner mandrel may be thicker and, therefore, less flexible than the section sealing the medicament reservoir. Where the sealing means is formed integral with the mandrel the V may be formed by a flap extending from the mandrel.

The proportion of the circumference of the mandrel sealed by the sealing means should be as high as possible, with the gap in the sealing means being sized to accommodate the pathway between the medicament reservoir and the inhalation chamber. Preferably the sealing ring should extend for about 250°–330° around the mandrel and more preferably for about 300°.

Since the sealing ring is formed from resilient material it can be held in position during assembly of the device by this resilience. During use axial and rotational movement may be constrained by shoulder features on the mandrel collar. Additionally, or alternatively, the sealing ring may be held in position by an adhesive bond between the sealing ring and the mandrel.

Thus, according to a further aspect of the invention there is provided a sealing means comprising a partial ring extending about 250°–330°, preferably about 300°, of a full ring circumference, whose cross section is generally V shaped.

The present invention is related to devices described in EP 407028 and EP 691865 which are hereby incorporated by reference. An embodiment of the present invention will now be described by way of example, with reference to the following drawings, in which.

Figure 1:
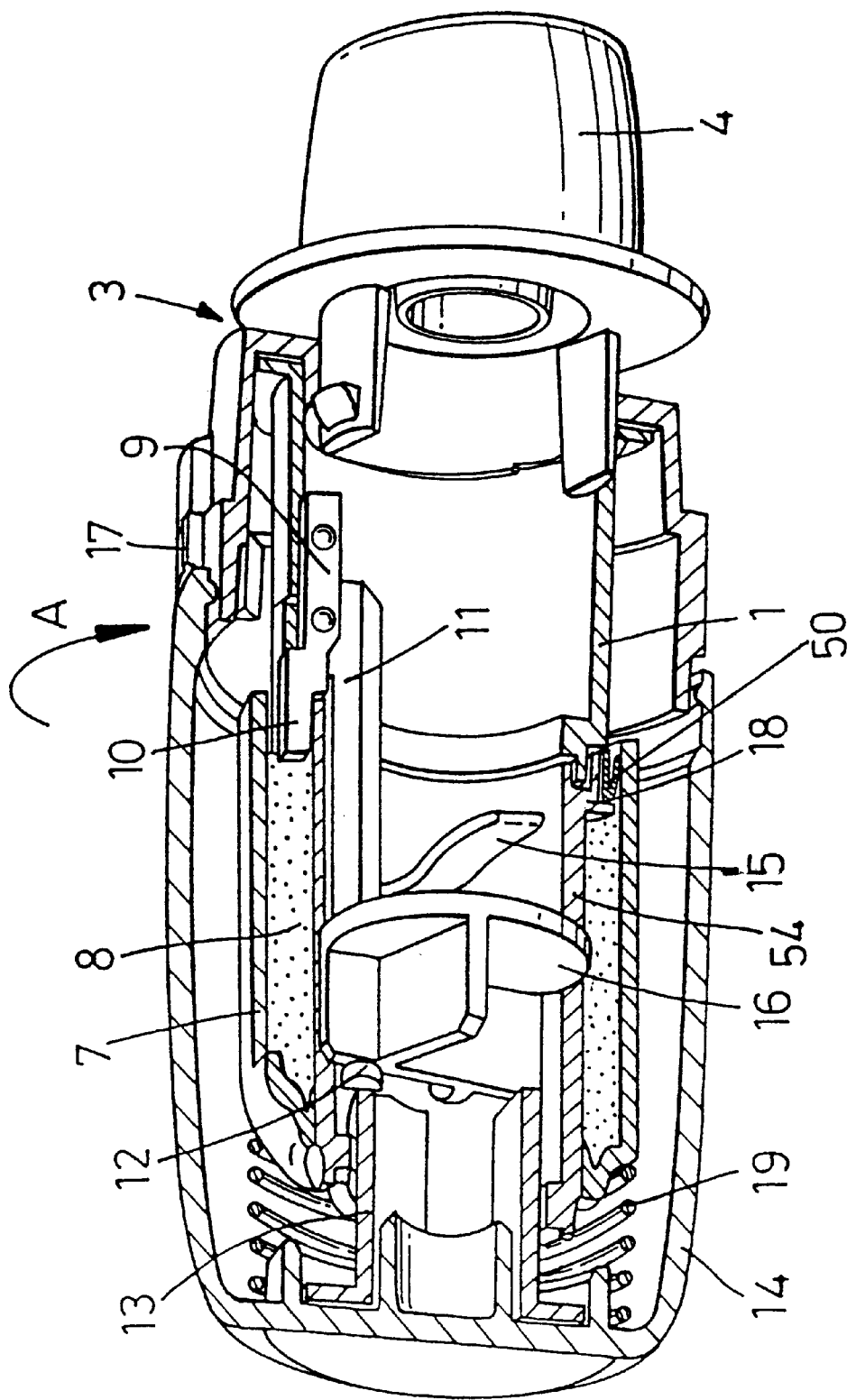
FIG. 1 is a longitudinal view in partial section of a device according to the present invention.

A device according to the invention includes a housing (1) having a mandrel (54) and a through-going pathway (2) connecting an air inlet (3) with an air outlet in the form of mouthpiece (4). A dispersion chamber (5) having tangential air inlets (6,6a) is located in the through-going pathway between air inlet (3) and mouthpiece (4). A generally cylindrical medicament reservoir (7) containing an annular compacted body of powdered inhalation medicament (8) is rotatably mounted on the mandrel (54) adjacent to the through-going pathway (2) up stream from the dispersion chamber (5). Sealing ring (50) is mounted between medicament reservoir (7) and a housing collar (55) located on mandrel (54), being constrained from rotation and axial movement by shoulder features (52,53) on the mandrel collar (55).

A shutter (9) comprising a metal blade (10) is mounted on a carrier (11) which is adapted to move axially within the housing between a first/rest position in which the compacted body (8) is isolated from the through-going pathway (2), and a second/metering position in which the compacted body (8) is in communication with the through-going pathway (2). The end of carrier (11) remote from the shutter (9) is provided with a lug (12) adapted to interact with a cam (13) provided on the inside of a drive sleeve (14) rotatably mounted on the housing (1). The carrier (11) is biased against the cam (13) by a half cantilever (15) provided on the carrier (11) which bears against an exterior wall of the dispersion chamber (5). The end of the carrier (11) remote from the shutter (9) is also provided with a disc (16) having a diameter generally corresponding to that of the interior of the housing (1). Disc (16) thus separates the cam (13) and reservoir drive mechanism (described below) from the through-going pathway (2) thus reducing the risk of ingress of medicament into the drive mechanism.

Drive sleeve (14) is also provided with a reservoir drive mechanism (not shown) which is adapted to rotate the medicament reservoir (7) through a predetermined angle relative to the housing (1), the angle of rotation being limited by a stop (17) provided on the exterior of the housing.

Figure 4:
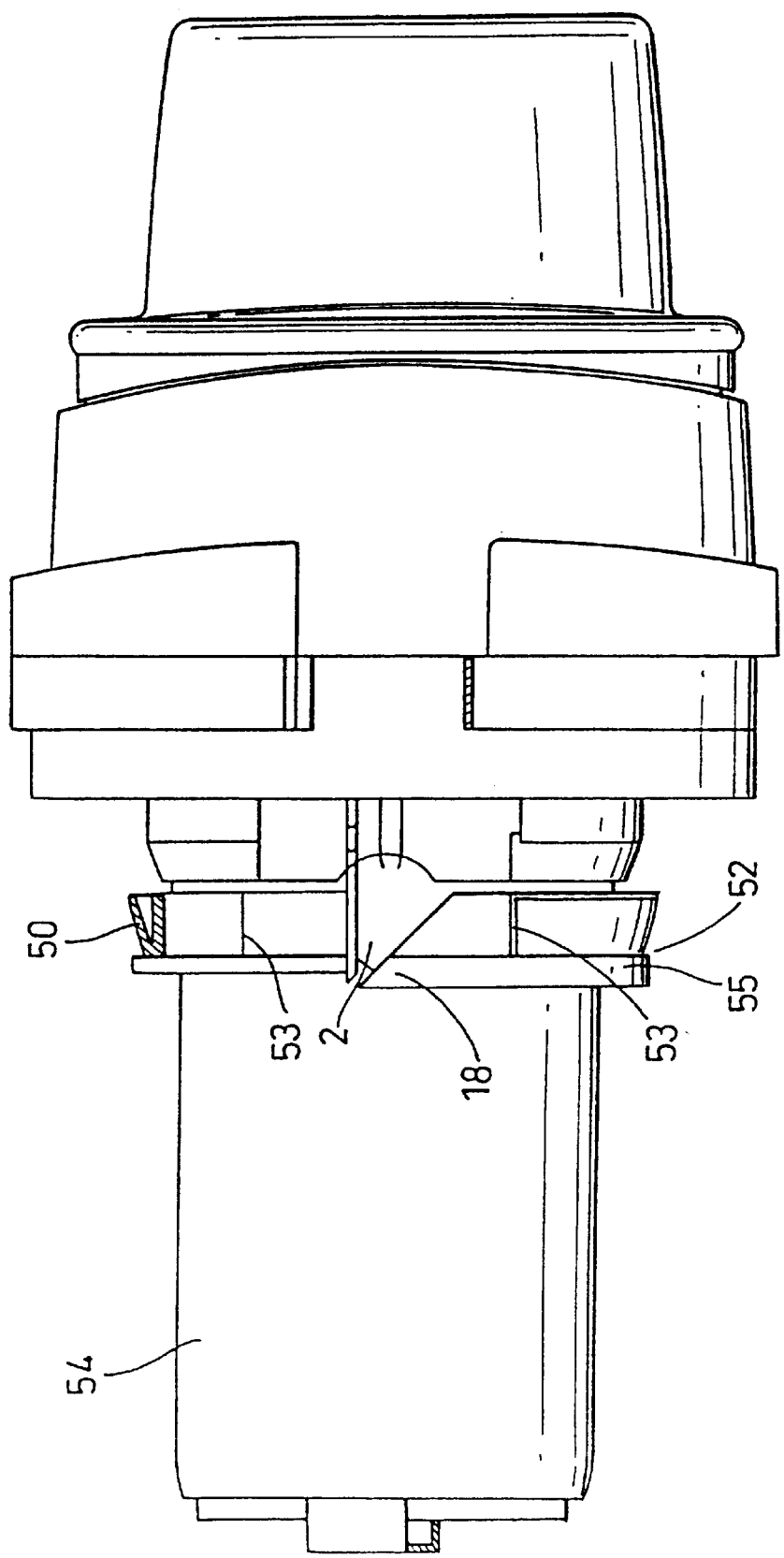
FIG. 4 is a longitudinal section of a portion of the device of FIG. 3 showing the position of the sealing ring and shoulder features.
Figure 5:
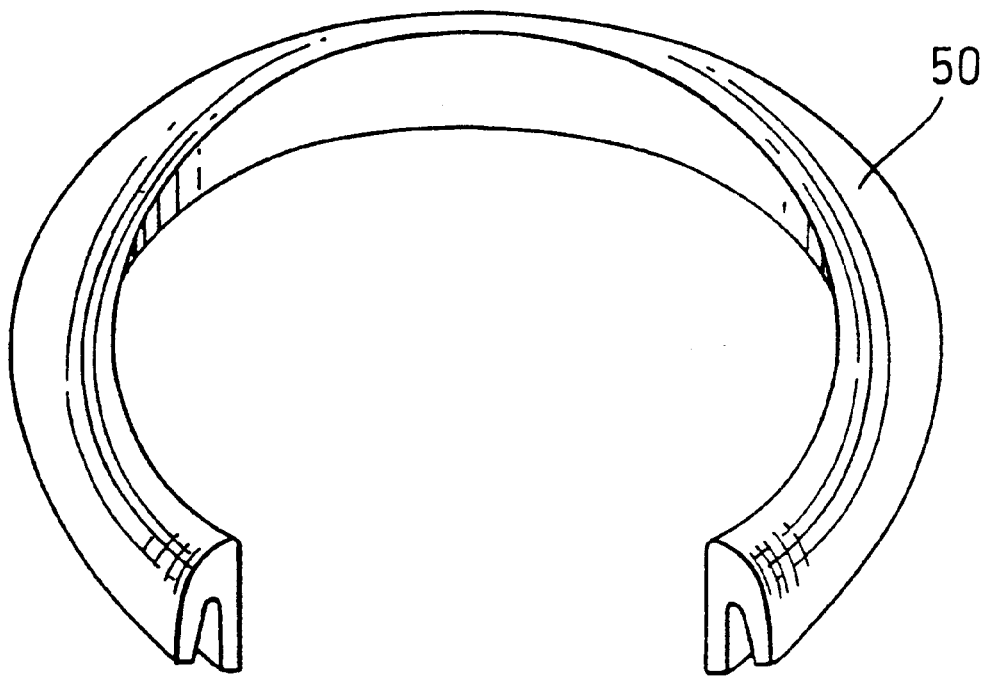
FIG. 5 is a perspective view of a sealing ring according to a preferred embodiment of the invention.

A helical blade (18) is fixedly mounted on the mandrel of the housing between the reservoir (7) and the mouthpiece (4), such that the blade (18) abuts against the face of the body of compacted medicament (8) contained in the reservoir (7). Blade (18) comprises the upper surface of collar (55) as best shown in FIG. 4. The body of compacted medicament (8) is further urged towards blade (18) by a compression spring (19) which acts against the outer wall of medicament reservoir (5) and the interior of drive sleeve (14).

In use, drive sleeve (14) is rotated in the direction of arrow A in FIG. 1. The initial part of the rotation causes the cam (13) to move carrier (11) axially within the housing (1) towards the mouthpiece (4). The shutter (9) thus moves from the first/rest position [FIG. 1] to the second/metering position [FIG. 2]. Once the compacted body (7) is in communication with the through-going pathway (2), further rotation operates the reservoir drive means (not shown) thus advancing the reservoir (7) and compacted body (8) through an angle of 60°, the degree of rotation being limited by stop (17) provided on the outside of the housing (1). As the reservoir (7) rotates helical blade (18) abrades a predetermined quantity of powdered medicament from the face of compacted body (8).

Figure 2:
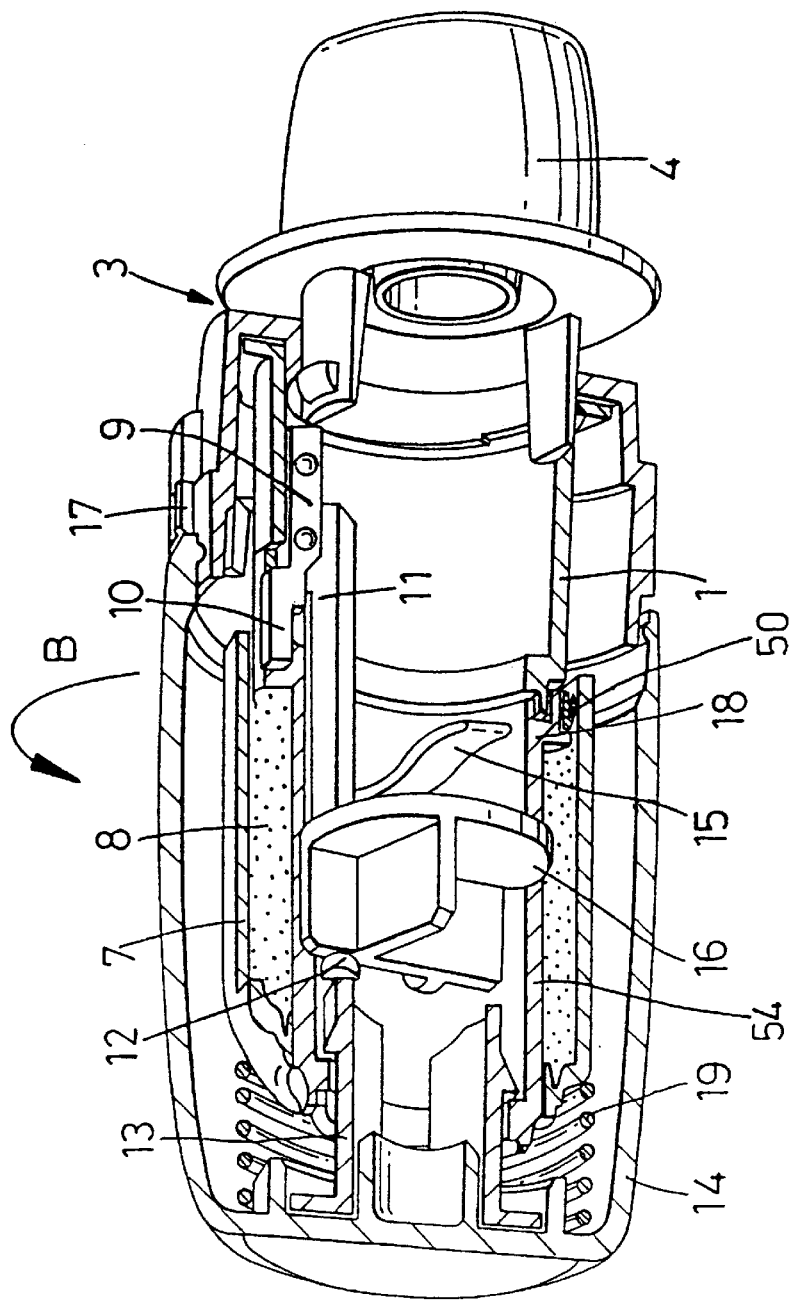
FIG. 2 is a longitudinal view in partial section of the device of FIG. 1 in the second metering position.
Figure 3:
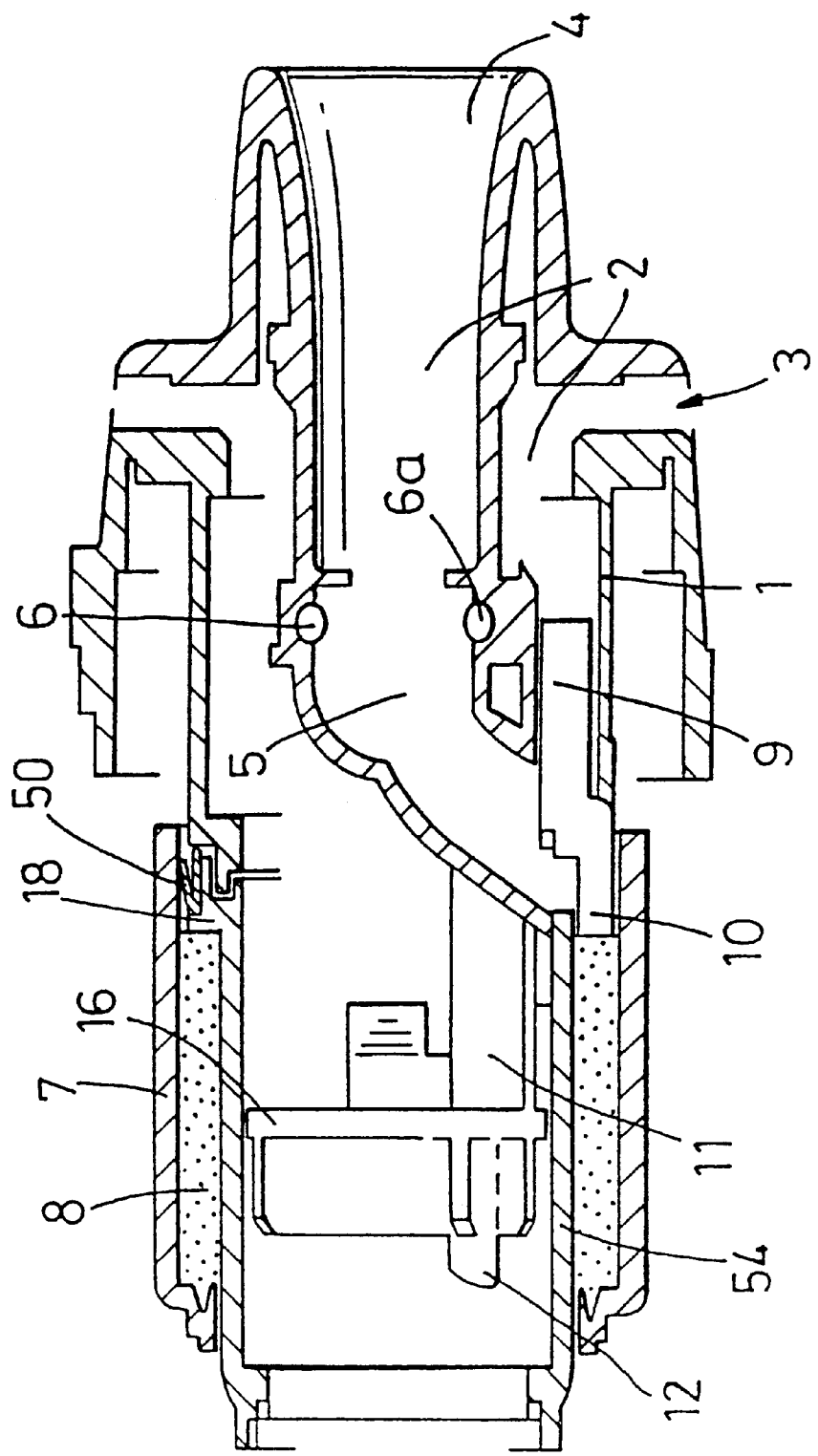
FIG. 3 is a longitudinal section showing in detail the position of the sealing ring and through-going pathway of a device according to the invention in the first/rest position.

The drive sleeve (14) is then rotated in the direct of arrow B in FIG. 2, Cam surface (13) rotates back to its original position allowing the shutter (9) to return to its first/rest position under the bias of cantilever (15). Friction between the sealing ring (50) and medicament reservoir (7) prevents any tendency for the medicament reservoir to move in direction B as drive sleeve (14) is returned to the starting position. As the shutter (9) returns to the first/rest position the metal blade (10) severs the abraded dose of medicament from the compacted body (8), the dose being deposited in the through-going pathway (2). The patient then inhales at the mouthpiece (4) drawing air through air inlet (3) and through-going pathway (2).

The dose of medicament is drawn into dispersion chamber (5) where it is entrained in the air flow and inhaled by the patient. During inhalation the shutter (9) prevents additional medicament from being scoured from the compacted body (8) since it, isolates the compacted body (8) from the through-going pathway (2).

EXAMPLE

Devices as described above were filled with a powder compact comprising medicament and lactose. One set was filled with a composition consisting, of Nedocromil Sodium, lactose and flavouring. A second set was filled with a composition consisting of Salbutamol and lactose. The devices were tested as follows. The device was actuated as described above to place a metered dose of medicament in the through going pathway (2). This dose was removed from the pathway and its weight measured. The device was then placed in a mechanical shaker and shaken vigorously for some minutes. The device was then visually inspected for powder leakage. If this was found to be excessive the device was failed. The test was repeated until the device failed or until the powder compact was exhausted.

Devices containing Nedocromil Sodium compacts failed after 1–5 actuations with no seal present. The tests were repeated with two seals according to the present invention.

In the first test a seal composed of ABS rubber was used. This had a generally U shape with the base of the U much thicker than the anus and the base of the U facing the powder compact. The seal extended 305° around the circumference of the mandrel.

In the second test a seal composed of polypropylene was used. The grade used was Novelen 248TC supplied by Targor. This seal had a generally V shaped cross section with the point of the V facing towards the powder compact. The seal extended 295° around the circumference of the mandrel.

All devices tested delivered in excess of 100 doses of medicament, which exhausted the medicament compact.

Devices containing Salbutamol compacts also failed after 1–5 actuations with no seal. With a seal composed of polypropylene as described above for Nedocromil Sodium the devices delivered between 73 and 158 doses before failing. The maximum number of doses possible was around 200.

What is claimed is:

1. In a medicament inhalation device including a housing having a through-going pathway connecting an air inlet with an air outlet, a medicament reservoir adapted to receive a compacted body of powdered medicament, an inner mandrel around which the medicament reservoir rotates and metering means for dispensing a predetermined dose of medicament from the reservoir into the pathway, the metering means including means for abrading the compacted body; the improvement wherein there is provided between the medicament reservoir and the inner mandrel of the device a sealing means extending round less than 360° of the mandrel.

2. A medicament inhalation device according to claim 1 in which the sealing means comprise a feature forming an integral part of the inner mandrel of the device.

3. A medicament inhalation device according to claim 1 in which the sealing means comprise a feature formed on the inner mandrel of the device during production of the inner mandrel.

4. A medicament inhalation device according to claim 1 in which the sealing means comprise a separate partial sealing ring.

5. A medicament inhalation device according to claim 1 which includes a ratchet mechanism designed to cause rotation of the medicament reservoir when said ratchet mechanism is moved from its starting position.

6. A medicament inhalation device according to claim 5 in which the sealing means is adapted to provide a frictional braking force on the medicament reservoir sufficient to prevent movement of the medicament reservoir when the ratchet mechanism, designed to cause rotation of the reservoir, is returning to its starting position, but which force is not so large as to make the device difficult to operate by a child or infirm adult.

7. A medicament inhalation device according to claim 6 in which the frictional braking force is in the range of 0.1–0.6 Nm torque.

8. A medicament inhalation device according to claim 1 in which the sealing means has a generally V shaped cross section.

9. A medicament inhalation device according to claim 1 in which the sealing means extends for about 250° to 330° around the mandrel.

10. A medicament inhalation device according to claim 1 in which the sealing means extends about 300° around the mandrel.

11. A medicament inhalation device according to claim 1 in which the sealing means is constructed from a polyolefin material.

12. A medicament inhalation device according to claim 1 in which the sealing means is constructed from polypropylene.

13. In a medicament inhalation device including a housing having a through-going pathway connecting an air inlet with an air outlet, a medicament reservoir containing a compacted body of powdered medicament, an inner mandrel around which the medicament reservoir rotates and metering means for dispensing a predetermined dose of medicament from the reservoir into the pathway, the metering means including means for abrading the compacted body; the improvement wherein there is provided between the medicament reservoir and the inner mandrel of the device a sealing means extending round less than 360° of the mandrel.

14. A sealing means adapted for use in an inhaler, said sealing means comprising a partial ring extending about 250°–330° of a full ring circumference whose cross section is generally V shaped.

15. A sealing means adapted for use in an inhaler, said sealing means comprising a partial ring extending 300° of a full ring circumference whose cross section is generally V shaped.

* * * * *